United States Patent [19]

Mochida et al.

[11] 4,237,272

[45] Dec. 2, 1980

[54] DERIVATIVES OF FORTIMICIN A

[75] Inventors: Kenichi Mochida, Hiratsuka; Moriyuki Sato; Shigeo Yoshiie, both of Machida; Yasuki Mori, Kawasaki, all of Japan

[73] Assignee: Kyowa Hakko Kogyo Co., Ltd., Tokyo, Japan

[21] Appl. No.: 971,438

[22] Filed: Dec. 20, 1978

[30] Foreign Application Priority Data

Dec. 21, 1977 [JP] Japan .................................. 52/153001

[51] Int. Cl.³ ........................ A61K 31/71; C07H 15/22
[52] U.S. Cl. .................................. 536/17 R; 424/180; 536/4

[58] Field of Search ................................... 536/17 R, 4

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 4,124,756 | 11/1978 | Martin et al. | 536/17 |

*Primary Examiner*—Johnnie R. Brown
*Attorney, Agent, or Firm*—Fitzpatrick, Cella, Harper & Scinto

[57] ABSTRACT

Semisynthetic antibacterial compounds are produced by chemically modifying the antibacterial compound fortimicin A.

4 Claims, No Drawings

DERIVATIVES OF FORTIMICIN A

BACKGROUND OF THE INVENTION

The present invention relates to novel derivatives of fortimicin A, the acid addition salts thereof and a process for preparing the same.

Fortimicins (A, B and C) are compounds belonging to pseudodisaccharide antibiotics containing 1,4-diaminocyclitol. The physical properties and antibacterial activities of these compounds, the processes for producing them by using microorganisms, and processes for separation and purification thereof from culture liquors, etc. are described in detail in U.S. Pat. Nos. 3,931,400, 3,976,768 and 4,048,015.

The planar structural formulae of the fortimicins, are illustrated in said United States Patents and their structural formulae showing absolute coordination are described in the specification of Japanese Published Unexamined Patent Application No. 50140/78.

Fortimicins (A, B and C) all have antibacterial activity, but the antibacterial activity of fortimicin B is not as good as the other factors; and fortimicin A and fortimicin C are slightly unstable under strongly alkaline conditions. Therefore, compounds having more distinguished properties are in demand.

As a result of various studies, it has been found that certain 4-N-substituted derivatives of fortimicin B have enhanced antibacterial activity and good stability under alkaline conditions (Japanese Published Unexamined Patent Application No. 50140/78).

Moreover, it has now been found that 2'-N-substituted derivatives of fortimicin A have an excellent antibacterial activity and further that the derivatives have a strong antibacterial activity against the strains resistant to fortimicin A.

SUMMARY OF THE INVENTION

The present invention relates to 2'-N-substituted derivatives of fortimicin A represented by the general formula (I):

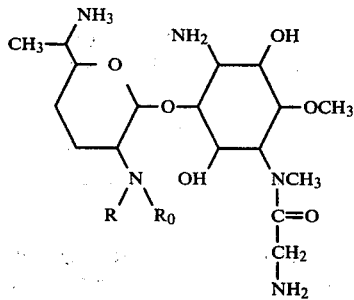

[wherein $R_0$ represents a hydrogen atom or $R_0$ forms, together with a nitrogen atom and R, a substituted or unsubstituted 2-pyrrolidonyl group (substituents are $1 \sim 2$ hydroxyl or amino groups and are bonded to the 3- or 4-position of the pyrrolidonyl group), and R represents $-COR_1$, $-CH_2R_1'$, $-CH(R_1')_2$ or an amidino group, wherein $R_1$ is an amino group, hydroxyaminoalkyl group or carbamoylaminoalkyl group and $R_1'$ is a diaminoalkyl group, hydroxyalkyl group, dihydroxyalkyl group, hydroxyaminoalkyl group or guanidinoalkyl group].

Included in the composition of matter aspect of the invention are the non-toxic acid addition salts of the compounds of the above general formula.

DETAILED DESCRIPTION

Compounds of the present invention are 2'-N-substituted derivatives of fortimicin A represented by the general formula (I):

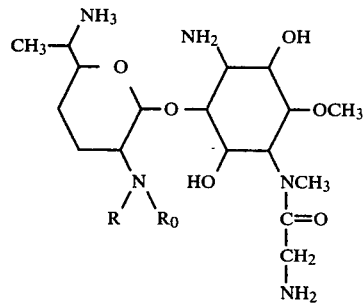

[wherein $R_0$ represents a hydrogen atom or $R_0$ forms, together with a nitrogen atom and R, a substituted or unsubstituted 2-pyrrolidonyl group (substituents are $1 \sim 2$ hydroxyl or amino groups and are bonded to the 3- or 4-position of the pyrrolidonyl group), and R represents $-COR_1$, $-CH_2R_1'$, $-CH(R_1')_2$ or an amidino group, wherein $R_1$ is an amino group, hydroxyaminoalkyl group or carbamoylaminoalkyl group and $R_1'$ is a diaminoalkyl group, hydroxyalkyl group, dihydroxyalkyl group, hydroxyaminoalkyl group or guanidinoalkyl group] and the pharmaceutically acceptable acid addition salts thereof.

The compounds of the present invention and their properties and Rf values in a thin layer chromatography are illustrated in Table 1. For comparison the data on fortimicin A are given in Table 1. In a thin layer chromatography silica gel plate (DC Fertigplatten Kieselgel 60 $F_{254}$ produced by E. Merck & Co., Inc.) is used and development is carried out using lower layer of methanol:chloroform:28% aqueous ammonia=1:1:1 (by volume). Coloring reaction is carried out with ninhydrin.

The nuclear magnetic resonance spectrum and mass spectrum of these compounds are shown in Examples.

The antibacterial activity of the present compounds are determined and the results are shown in Table 2. The determination is carried out according to the Japanese Antibiotic Medicament Standard using a medium having a pH of 7.2. The numbers indicate minimum inhibitory concentrations (MIC, mcg/ml). The compound numbers correspond to those in Table 1.

TABLE 1

| No. | Compound | $R_0$ in the general formula (I) | R in the general formula (I) | Specific rotation | Rf |
|---|---|---|---|---|---|
| 1 | fortimicin A | H | H | $[\alpha]_D^{25} = +26$[*1] | 0.61 |
| 2 | 2'-N-hydantoyl fortimicin A | H | $-COCH_2NHCNH_2$ $\parallel$ $O$ | $[\alpha]_D^{23} = +103.0$[*1] | 0.41 |
| 3 | 2'-N-carbamoyl | H | $-CONH_2$ | $[\alpha]_D^{21.5} = +116.0$[*2] | 0.56 |

TABLE 1-continued

| No. | Compound | $R_0$ in the general formula (I) | R in the general formula (I) | Specific rotation | Rf |
|---|---|---|---|---|---|
| 4 | 2'-N-amidino fortimicin A | H | $-\underset{\underset{NH}{\parallel}}{C}-NH_2$ | $[\alpha]_D^{21.5} = +65.0$[*1] | 0.13 |
| 5 | 2'-N-[(S)-2-amino-4-hydroxybutyl] fortimicin A | H | $-CH_2\underset{\underset{NH_2}{\mid}}{CH}CH_2CH_2OH$ | $[\alpha]_D^{21} = +84.5$[*2] | 0.54 |
| 6 | 2'-N-[(S)-2,4-diaminobutyl] fortimicin A | H | $-CH_2\underset{\underset{NH_2}{\mid}}{CH}CH_2CH_2NH_2$ | $[\alpha]_D^{21} = +55.5$[*1] | 0.35 |
| 7 | 2'-N-[(S)-2-amino-3-hydroxypropyl] fortimicin A | H | $-CH_2\underset{\underset{NH_2}{\mid}}{CH}CH_2OH$ | $[\alpha]_D^{21} = +57.5$[*1] | 0.50 |
| 8 | 2'-N-(2,3-dihydroxypropyl) fortimicin A | H | $-CH_2\underset{\underset{OH}{\mid}}{CH}CH_2OH$ | $[\alpha]_D^{21.5} = +70.0$[*1] | 0.52 |
| 9 | 2'-N-2-(1,3-dihydroxypropyl) fortimicin A | H | $-CH(CH_2OH)_2$ | $[\alpha]_D^{21.5} = +67.5$[*1] | 0.48 |
| 10 | 2'-N-(2-guanidinoethyl) fortimicin A | H | $-CH_2CH_2NH\underset{\underset{NH}{\parallel}}{C}-NH_2$ | $[\alpha]_D^{21.5} = +48.5$[*1] | 0.14 |
| 11 | 2'-deamino-2'-[1-(4-amino-2-pyrrolidonyl)] fortimicin A | $R_0$ and R form 1-(2-pyrrolidonyl group | ![structure: pyrrolidone with NH2 at 4-position, N attached] | $[\alpha]_D^{21} = +131.5$[*2] | 0.67 |

[*1]Specific rotation of sulfate (C = 0.2, water)
[*2]Specific rotation of free base (C = 0.2, water)

TABLE 2

| Strain | 1 (fortimicin A) | 4 | 5 | 6 | 7 | 9 | 10 | 11 |
|---|---|---|---|---|---|---|---|---|
| Staphylococcus aureus 209-P | 1.56 | 1.56 | 1.5 | 6.25 | 3.12 | 6.25 | 3.12 | 1.56 |
| Staphylococcus aureus Smith | 0.78 | 0.78 | 0.78 | 3.12 | 0.78 | 1.56 | 0.78 | 0.78 |
| Bacillus subtilis ATCC-6633 | 0.78 | 0.78 | 0.78 | 3.12 | 0.78 | 1.56 | 0.78 | 0.40 |
| Escherichia coli NIHJC-2 | 3.12 | 6.25 | 3.12 | 6.25 | 6.25 | 12.5 | 6.25 | 1.56 |
| Escherichia coli 3100 | 6.25 | 6.25 | 6.25 | 12.5 | 12.5 | 6.25 | 6.25 | 1.56 |
| Klebsiella pneumoniae #8045 | 1.56 | 1.56 | 1.56 | 3.12 | 3.12 | 6.25 | 3.12 | 0.78 |
| Shigella sonnei ATCC-9290 | 12.5 | 12.5 | 12.5 | 50 | 25 | 25 | 12.5 | 12.5 |
| Providencia sp. KY 3950 | 25 | 25 | 25 | 50 | 50 | 50 | 25 | 3.12 |
| Pseudomonas aeruginosa BMH #10 | 0.78 | 1.56 | 0.78 | 3.12 | 1.56 | 3.12 | 1.56 | 0.78 |
| Escherichia coli Z-343 *1 | 1.56 | 1.56 | 1.56 | 12.5 | 3.12 | 6.25 | 1.56 | 1.56 |
| Escherichia coli KY 8321 *2 | 12.5 | 6.25 | 6.25 | 12.5 | 6.25 | 25 | 6.25 | 1.56 |
| Escherichia coli KY 8348 *3 | >100 | 3.12 | 3.12 | 12.5 | 12.5 | >100 | 12.5 | 0.78 |
| Escherichia coli 57R/W677 *4 | 6.25 | 6.25 | 1.56 | 12.5 | 6.25 | 25 | 6.25 | 3.12 |
| Pseudomonas aeruginosa KY 8511 *3 | >100 | 50 | 100 | 50 | >100 | >100 | 100 | 50 |
| Pseudomonas aeruginosa KY 8516 *1 | 25 | 12.5 | 50 | 25 | 25 | 50 | 12.5 | 6.25 |
| Providencia sp. 164 *5 | 25 | 25 | 25 | 50 | 50 | 25 | 12.5 | 6.25 |
| Klebsiella pneumoniae 3020Y60 *4 | 12.5 | 12.5 | 6.25 | 12.5 | 12.5 | 50 | 12.5 | 6.25 |

The strains inactivate antibiotics with the above enzymes produced.

As apparent from the above results, the compounds of the present invention have a strong antibacterial activity against various microorganisms and therefore are expected to be useful as antibacterial agents and disinfectants. The nontoxic acid addition salts of the present compounds have a broad range of antibacterial spectrum and are useful as antibacterial agents, etc. The non-toxic acid addition salts of the present invention include the salts of hydrochloric acid, sulfuric acid, hydrobromic acid, amidosulfonic acid, phosphoric acid, maleic acid, acetic acid, citric acid, oxalic acid, succinic acid, benzoic acid, fumaric acid, malic acid, mandelic acid, ascorbic acid, etc.

The process for producing the compounds of the present invention is described below.

The compounds of the present invention are produced according to the steps of Flow Sheets 1-3. The main synthesis routes of the desired compounds of the present invention, i.e. Compounds (I) represented by the general formula (I) are (A) the steps 1, 2, 5 and 7
(B) the steps 1, 3, 4, 6 and 8
(C) the steps 1, 2, 5, 9, 10 and 11
(D) the steps 1, 2, 5, 9, 1 and 7, etc.

In the present specification, the compounds represented by the general formula (X=I, II, III, IV, V, VI, VII, X, XI-1, XI-2 and XII) are respectively referred to as Compounds (X=I, II, III, IV, V, VI, VII, X, XI-1, XI-2 and XII).

When R in Compounds (I) is represented by $-COR_1$, Compounds (I) are mainly synthesized by the route (A), but can be also synthesized by the route (D). The route (D) is an advantageous process on a laboratory scale.

When R in Compounds (I) is represented by —CH$_2$R$_1$' (wherein R$_1$' has the same meaning as defined above), Compounds (I) are synthesized by the route (B) or the route (C).

When R in Compounds (I) is represented by —CH(R$_1$')$_2$, Compounds (I) are synthesized by the route (C). In this case, 1,6'-diprotected-4-N-(N-protected glycyl) fortimicin B [Compounds (X)] is used as a intermediate.

In order to synthesize Compounds (X), it is convenient to prepare Compounds (III) having a different amino-protecting group releasable by a different method at the 2'-position and 1- and 6'-positions respectively. Preferable amino-protecting groups are benzyloxycarbonyl group and t-butoxycarbonyl group.

When R$_0$ in Compounds (I) forms a ring together with a nitrogen atom and R, Compounds (I) are synthesized by the route (B).

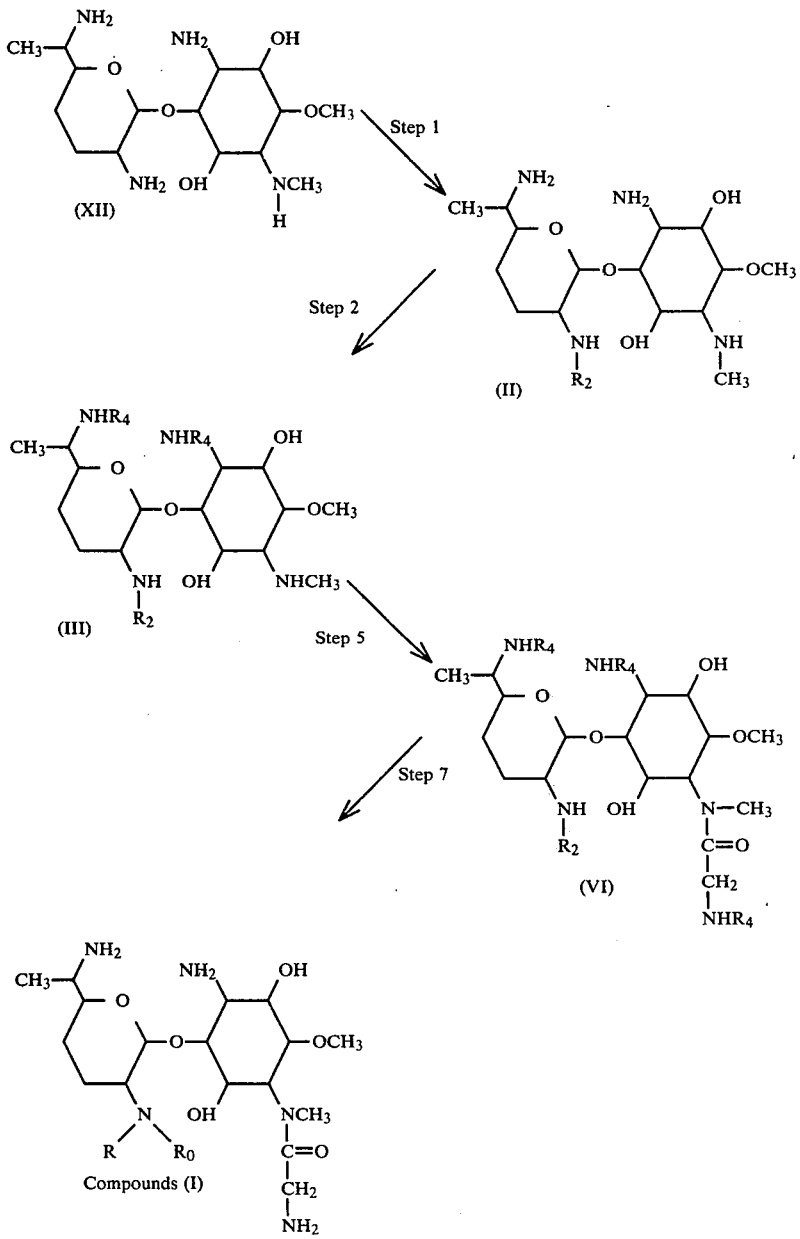

Flow Sheet 2
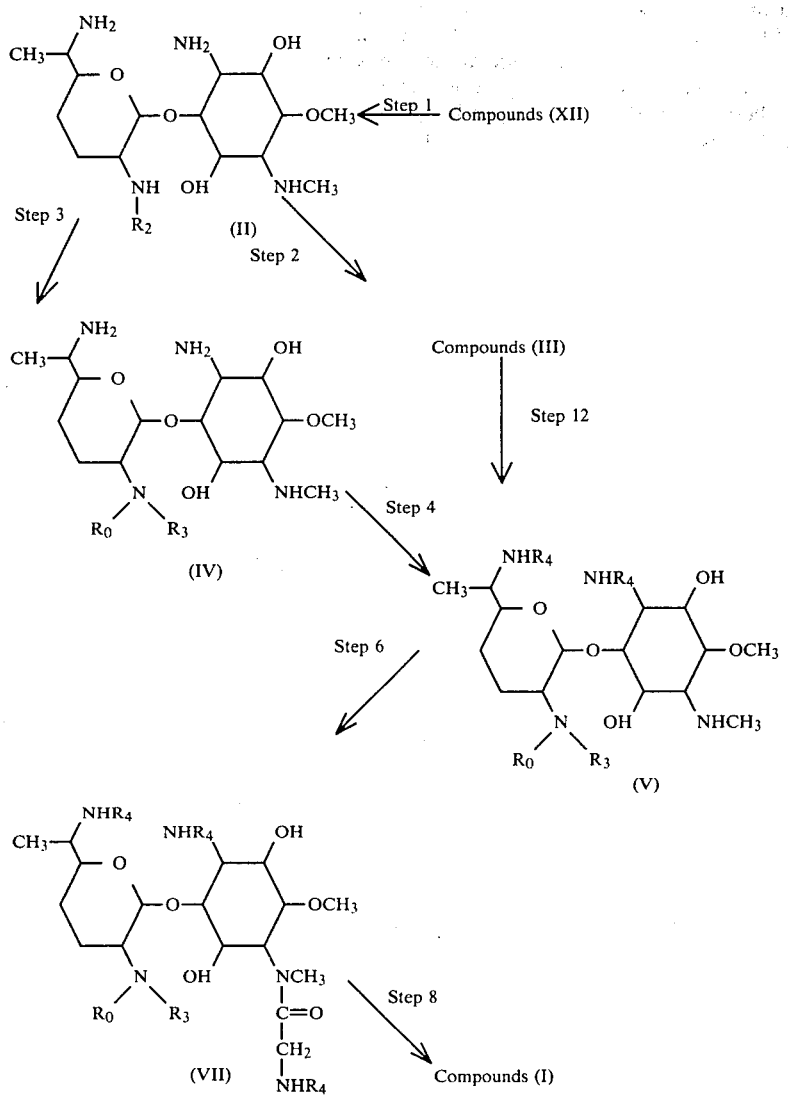
Flow Sheet 3
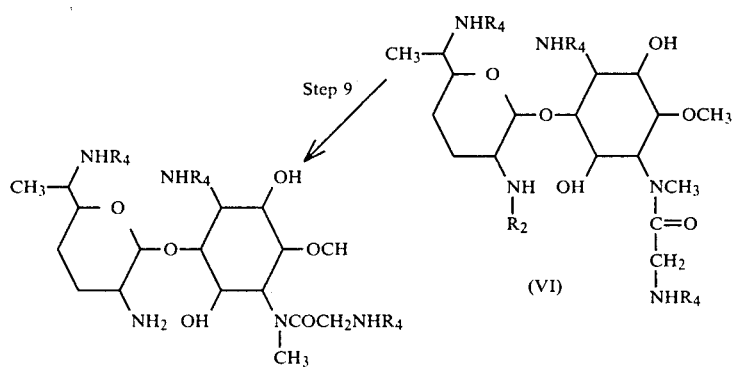

-continued

Flow Sheet 3

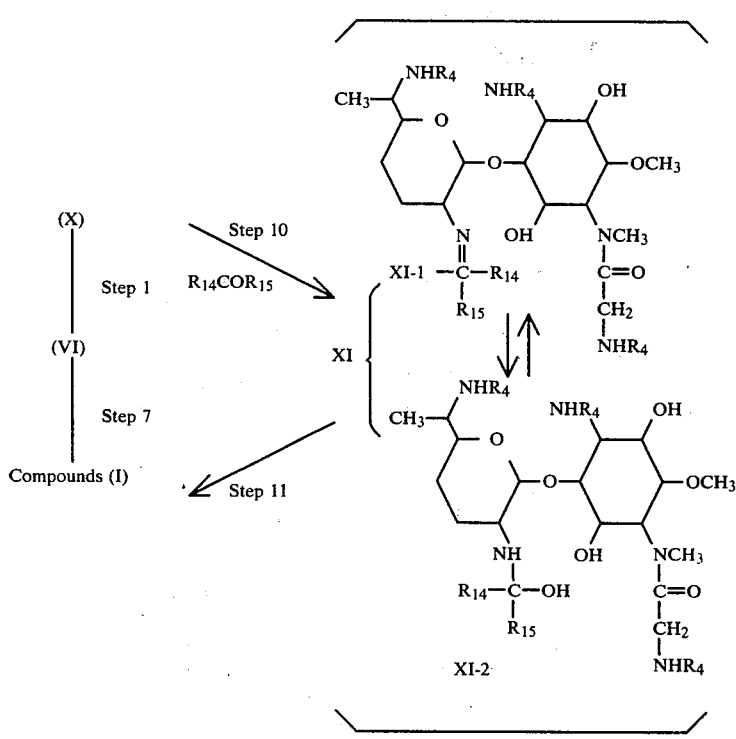

The above steps are explained in detail below.

Step 1

Synthesis of Compounds (II) represented by the general formula (II) from fortimicin B represented by the formula (XII)

Compound (II) can be obtained by acylation of formtimicin B using carboxylic acid represented by the general formula $R_2$-OH or its derivatives functionally equivalent thereto. $R_2$ represents an acyl group having 2 to 9 carbon atoms, a hydroxyacyl group having 2 to 6 carbon atoms, an alkoxyacyl group having 2 to 6 carbon atoms, a carbamoylaminoacyl group having 3 to 10 carbon atoms, a substituted aminoacyl group having 5 to 17 carbon atoms (substituent is an amino-protecting group), a substituted aminohydroxyacyl group having 5 to 17 carbon atoms (substituent is an amino-protecting group), a substituted amino-carbamolyacyl group having 3 to 17 carbon atoms, an N-alkylaminohydroxyacyl group having 3 to 9 atoms, a substituted aminoalkoxycarbonylacyl group having 5 to 17 carbon atoms (substituent is an amino-protecting group), an alkoxycarbonyl group having 5 to 10 carbon atoms or an aralkoxycarbonyl group having 8 to 13 carbon atoms.

When $R_2$ is an alkoxycarbonyl group aralkoxycarbonyl group, an amino-protecting reagent, which is usually used in peptide synthesis, may be used for the acylation of fortimicin B.

Examples of preferable amino-protecting reagent are shown below.

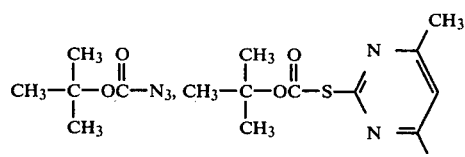

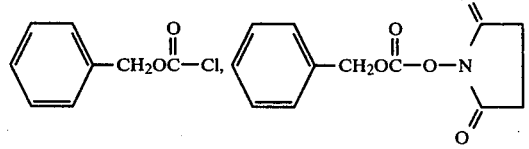

As the carboxylic acid derivatives functionally equivalent to carboxylic acid represented by $R_2$-OH which are used for the acylation, anhydride, active ester, acid halides, etc. of carboxylic acid may be used.

As active esters, the active esters of said carboxylic acid with one of the compounds represented by

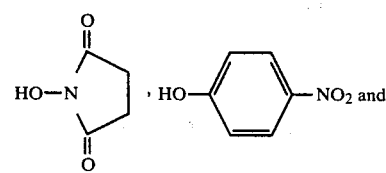

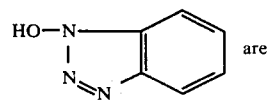

are preferred. The most preferable active ester is an active ester

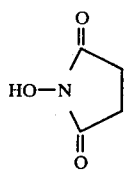

As the reaction solvents dimethylformamide, tetrahydrofuran, dioxane, methanol, ethanol, acetone, water and mixtures thereof may be used. Among these solvents, methanol and a mixture of tetrahydrofuran and water (1:1 by volume) are suitable. The concentration of fortimicin B to be used for the reaction is preferably 5–100 mmoles. The suitable amount of acylating agent is 1–2 moles per mole of fortimicin B. Reaction time is usually 1–24 hours. Reaction temperature is 0°–60° C., preferably 0° C. to room temperature.

Compounds (II) synthesized by the above method are purified and isolated according to the following procedure. The solvent is removed from the reaction mixture by distillation and to the residue is added an equal amount of water to that of the solvent before distillation. The resulting solution is adjusted to pH 5–6 with alkali or acid, and then passed through a column packed with a weakly acidic ion-exchange resin [for example, Amberlite CG-50 ($NH_4^+$ form) (Rohm & Haas Co. Ltd., trade name)]. After washing the column with water, elution is carried out with 0.01–1 N aqueous ammonia. Fractions containing Compounds (II) are combined and aqueous ammonia is removed therefrom by distillation to obtain the desired compound as a white powder. The desired compound is detected by a silica gel thin layer chromatography using lower layer of chloroform:methanol:14% aqueous ammonia=2:1:1 (by volume) as the developer.

Step 2

Synthesis of Compounds (III) represented by the general formula (III) from Compounds (II) represented by the general formula (II)

Compounds (III) are obtained by reacting Compounds (II) with an amino-protecting reagent in an appropriate solvent. Compounds (III) are the compounds wherein the amino groups at the 1- and 6'-positions of Compounds (II) are protected with the amino-protecting group $R_4$.

In this reaction, the amino-protecting reagents represented by the following formulae are preferably used to introduce a t-butoxycarbonyl group.

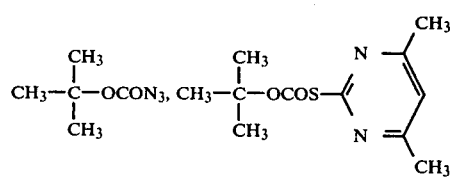

When a benzyloxycarbonyl group is introduced, the amino-protecting reagents represented by the following formulae are preferably used.

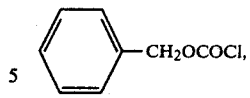

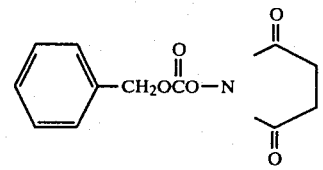

As solvent, tetrahydrofuran, dioxane, methanol, ethanol, chloroform, etc. may be used. Especially, tetrahydrofuran and chloroform are preferred. The concentration of Compounds (II) to be used in the reaction is preferably 5–100 mmoles. The suitable amount of the amino-protecting reagent is 2–3 moles per mole of Compounds (II). Reacton temperature is 0°–60° C. and reaction time is usually 2–48 hours. Compounds (III) synthesized by the above method are isolated and purified according to the following procedure. The solvent is removed from the reaction mixture by distillation. To the resulting residue is added an equal amount of organic solvent such as ethyl acetate, chloroform, etc. to that of the solvent before distillation to extract the soluble part. Then, the extract is subjected to column chromatography using a silica gel. [for example, Kieselgel 60 (E. Merck & Co., Ltd., trade name)]. Elution is carried out with organic solvent such as chloroform: methanol (99:1~90:10 by volume) and the fractions containing Compounds (III) are combined. The desired compound is detected by a thin layer chromatography using chloroform:methanol (9:1 by volume) as the developer. The combined fractons are concentrated to dryness to obtain the desired compound as a white powder. On the other hand, Compounds (III) synthesized as above may be used in a subsequent step as the reaction mixture without isolation.

Step 3

Synthesis of the compounds represented by the general formula (IV) from the compounds represented by the general formula (II)

Compounds (IV) represented by the general formula (IV):

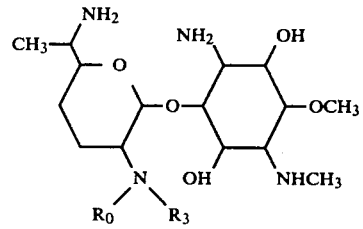

[wherein $R_0$ represents a hydrogen atom or $R_0$ forms, together with a nitrogen atom and $R_3$, a substituted or unsubstituted 2-pyrrolidonyl group (substituents are 1–2 hydroxyl or amino groups and are bonded to the 3- or 4-position of the pyrrolidonyl group), and $R_3$ represents an alkyl group, hydroxyalkyl group, substituted or unsubstituted aminoalkyl group (substituent is an amino-protecting group), carbamoylaminoalkyl group or substituted or unsubstituted aminohydroxyalkyl group (substituent is an amino-protecting group] are obtained by reducing Compounds (II) obtained in the step 1 in an appropriate solvent in the presence of a reducing agent at a temperature from room temperature to reflux temperature of the solvent.

Reducing agent is used for converting the carbonyl group of the amide group contained in the substituent $R_2$ in Compounds (II) to a methylene group. As reducing agent, usually 10 moles or more of lithium aluminum hydride, diborane, etc. per mole of Compounds (II) are used in excess of Compounds (II).

As solvent, tetrahydrofuran, dioxane and diethyl ether may be used. The concentration of Compounds (II) in the reaction mixture is preferably 1–100 mmoles. Reaction time is usually 3–18 hours. Isolation of Compounds (IV) from the reaction mixture is carried out in the following manner. The excess reducing agent in the reaction mixture is decomposed by adding 10 moles of ethyl acetate, water, etc. per mole of the reducing agent and most of the solvent is distilled away under reduced pressure. The resulting residue is adjusted to pH 5–6 with acid or alkali and 10 times as much water as the residue is added thereto to extract the water-soluble part. Then, the extract is passed through a column packed with a weakly acidic ion-exchange resin [for example, Amberlite CG-50 ($NH_4^+$ form)]. After the column is washed with water, elution is carried out with 0.1–1 N aqueous ammonia and the fractions containing the desired compound are combined. Aqueous ammonia is removed from the combined fractions under reduced pressure to obtain the compounds represented by the formula (IV) as a white powder. The desired compound is detected by a silica gel thin layer chromatography using lower layer of chloroform: methanol: 28% aqueous ammonia (1:1:1 by volume) or lower layer of chloroform: methanol: 14% aqueous ammonia (2:1:1 by volume) as the developer.

In the step 3, when there is an amino-protecting group in the substituent $R_3$, the amino-protecting group may be eliminated to facilitate confirmation of the chemical structure. In such a case, a protecting group can be introduced again by increasing the amount of the amino-protecting reagent used in the subsequent protection of the amino groups at the 1- and 6'-positions (the step 4).

Step 4

Synthesis of Compounds (V) represented by the general formula (V) from Compounds (IV) represented by the general formula (IV)

Componds (V) are obtained by reacting Compounds (IV) with an amino-protecting reagent in an appropriate solvent. Compounds (V) are the compound wherein the amino groups at the 1- and 6'-positions of Compounds (IV) are protected with an amino-protecting group.

The same reaction procedure using the same amino-protecting reagent and the same isolation and purification procedure as in the step 2 are repeated to obtain Compounds (V) as a white powder. The desired compound is detected by a thin layer chromatography using chloroform: methanol (9:1 or 19:1 by volume) as a developer.

2'-N-(2-guanidinoethyl) fortimicin A can be synthesized by reacting the compound obtained in the step 4 such as 2'-N-(2-aminoethyl)-1,6'-di-N-benzyloxycarbonyl fortimicin B with 1-nitroguanidyl-3,5-dimethyl-pyrazol to form 2'-N-(2-nitroguanidinoethyl)-1,6'-di-N-benzyloxycarbonyl fortimicin B, and then using the obtained compound as a raw material in the step 6.

Step 5

Synthesis of Compounds (IV) represented by the general formula (VI) from Compounds (III) represented by the general formula (III)

Compounds (VI) are obtained by subjecting Compounds (III) to condensation reaction with N-protected glycine represented by $R_4NHCH_2CO_2H$ in an appropriate solvent.

As the N-protecting group ($R_4$) of N-protected glycine, those which are usually used in peptide synthesis can be used, and preferably the same protecting group as in the step 2 is used. Condensation is carried out by condensation method used in peptide synthesis, preferably by active ester method. As active ester of N-protected glycine in active ester method, esters of N-protected glycine with

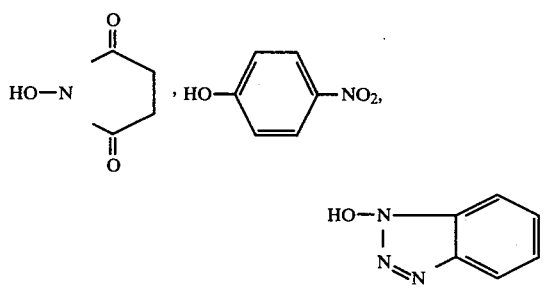

etc. may be used and especially an ester with

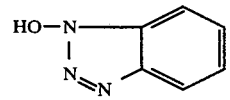

is preferred. The concentration of Compounds (III) is 10–100 mmoles. The reactive derivative of N-protected glycine activated at its carboxyl group is used in an amount of more than 1 mole per mole of Componds (III). For example, in case of active ester, 1–3 moles of ester is preferably used per mole of Compounds (III). As the solvent, dimethylformamide, tetrahydrofuran, dioxane and chloroform may be used. Reaction is carried out at a temperature of $-10°$ C. to room temperature for 15–20 hours.

Compounds (VI) formed in the reaction mixture by the above reaction are usually used in a subsequent step without isolation. Isolation may be carried out by column chromatography similar to that in the step 2, if desired. The desired compound is detected by a silica gel thin layer chromatography using chloroform: methanol (19:1 by volume) as the developer.

Step 6

Synthesis of Compounds (VII) represented by the general formula (VII) from Compounds (V) represented by the general formula (V)

Compounds (VII) represented by the general formula (VII) are obtained by treating Compounds (V) represented by the general formula (V) as the raw material in the same manner as in the step 5.

Step 7

Synthesis of Compounds (I) represented by the general formula (I) from Compounds (VI) represented by the general formula (VI)

Compounds (I) are obtained by eliminating the amino-protecting group $R_4$ in Compounds (VI) by a known method.

For example, when the amino-protecting group in Compounds (VI) is a benzyloxycarbonyl group, Compounds (VI) are subjected to catalytic reduction by blowing hydrogen gas through the reaction mixture in the presence of metal catalyst and acid at room temperature and at atmospheric pressure, whereby the amino-protecting group is eliminated. As solvent, methanol, tetrahydrofuran, dioxane, water and mixtures thereof may be used. As the metal catalyst, palladium carbon, platinum, etc. are used usually in an amount of 1–10 wt % to Compounds (VI). As the acid, hydrochloric acid, sulfuric acid, acetic acid, etc. may be used. The concentration of Compounds (VI) is usually 0.01–1 mole/l. Reaction time is generally 2–18 hours.

Compounds (I) represented by the general formula (I) are obtained as an acid addition salt thereof by filtering the reaction mixture and evaporating the resulting filtrate to dryness.

Purification is carried out in the following manner.

The acid addition salt obtained as above is dissolved in a small amount of water. The aqueous solution is passed through a column packed with a weakly acidic ion-exchange resin such as Amberlite CG-50 ($NH_4^+$ form) to adsorb the product on the resin. After the column is washed with 5–10 times as much water as the resin, elution is carried out with 0.1–1 N aqueous ammonia and the active fractions are combined. The solvent is removed therefrom by distillation to obtain the desired compound as a white powder.

The desired compound is detected by a silica gel thin layer chromatography using lower layer of chloroform: methanol: 28% aqueous ammonia (1:1:1 by volume) as the developer.

Further, when the amino-protecting group in Compounds (VI) is a t-butoxycarbonyl group, the amino-protecting group is eliminated by treating Compounds (VI) with an acid in an appropriate solvent. As the solvent, nonaqueous solvents such as dichloromethane, chloroform, ethyl acetate, etc. may be used. As the acid, hydrochloric acid, trifluoroacetic acid, etc. may be used in an amount of 20–100 moles per mole of Compounds (VI). The concentration of Compounds (VI) is usually 0.1–10 moles/l. Reaction is carried out at a temperature of 0° C. to room temperature usually for 30 minutes to 8 hours.

Step 8

Synthesis of Compounds (I) represented by the general formula (I) from Compounds (VII) represented by the general formula (VII)

Compounds (I) are obtained by eliminating the amino-protecting group $R_4$ in Compounds (VII) by a known method as in the step 7.

Step 9

Synthesis of the compounds represented by the general formula (X) from the compounds represented by the general formula (VI)

The compounds represented by the general formula (X) are obtained by eliminating the substituent $R_2$ bonded to the 2'-position of Compounds (VI) by a known method. Elimination is carried out in a similar manner as in the step 7.

In this step, Compounds (VI) wherein the substituent $R_2$ at the 2'-position is the amino-protecting group represented

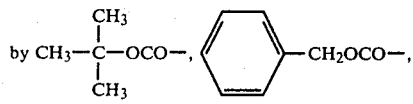

etc. are usually used as the raw material. Further, in this step, Compounds (VI) wherein the amino-protecting groups at the 1- and 6'-positions are different from that at the 2'-position are used as the raw material. For example, the compound wherein $R_2$ at the 2'-position is

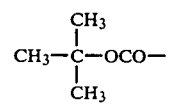

and the amino-protecting group $R_4$ at the 1- and 6'-positions is

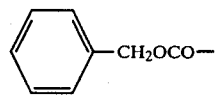

and the compond wherein $R_2$ at the 2'-position is

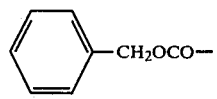

and the amino-protecting group $R_4$ at the 1- and 6'-positions is

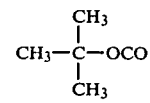

are preferably used.

2'-N-amidino fortimicin A is synthesized by reacting Compounds (X) obtained in the step 9 such as 1,6'-di-N-benzyloxycarbonyl-4-N-(N-benzyloxycarbonylglycyl) fortimicin B with 1-nitroguanidyl-3,5-dimethylpyrazol to form 2'-N-nitroamidino-1,6'-di-N-benzyloxycarbonyl 4-N-(N-benzyloxycarbonylglycyl) fortimicin B, and eliminating the protecting groups thereof (through the step 11).

2'-N-carbamoyl fortimicin A is synthesized by reacting Compounds (X) obtained in the step 9 such as 1,6'-di-N-benzyloxycarbonyl-4-N-(N-benzyloxycarbonylglycyl) fortimicin B with acetic acid and potassium cyanate, and eliminating the protecting groups thereof (through the step 11).

Step 10

Synthesis of the compounds represented by the general formula (XI) from the compounds represented by the general formula (X)

Compounds (XI) represented by the general formula (XI) are obtained by reacting Compounds (X) represented by the general formula (X) with an aldehyde or ketone represented by the general formula R$_{14}$COR$_{15}$ (wherein R$_{14}$ and R$_{15}$ may be the same or different and are a hydrogen atom, hydroxyalkyl group or dihydroxyalkyl group) in the presence of a reducing agent.

The obtained Compounds (XI) are usually converted to Compounds (I) without isolation.

As the aldehyde used in the reaction, aliphatic aldehyde having 1 to 16 carbon atoms, etc. are suitable, and as ketone, aliphatic ketone having 3 to 10 carbon atoms, etc. are suitable. Sodium boron hydride and sodium cyanoboron hydride may be used as the reducing agent. As the solvent, methanol, ethanol, tetrahydrofuran, dioxane, water and mixtures thereof may be used. Especially, methanol is preferred. The concentration of Compounds (X) to be used in the reaction is 10–100 mmoles.

The aldehyde, ketone and reducing agent are used in an amount of 1–50 moles per mole of Compounds (X). Reaction is carried out at a temperature of 0° C. to room temperature usually for 2–18 hours.

Step 11

Synthesis of Compounds (I) represented by general formula (I) from Compounds (XI) represented by the general formula (XI)

Compounds (I) are obtained by eliminating the amino-protecting group R$_4$ in Compounds (XI) obtained in the step 10 by a known method.

Usually, Compounds (XI) obtained in the step 10 are used as the raw material without isolation.

Reaction and purification are carried out in a similar manner as in the step 7.

For example, when the amino-protecting group in Compounds (XI) is a benzyloxycarbonyl group, the same procedure as in the step 7 is repeated adding metal catalyst after the completion of reaction of the step 10.

When the amino-protecting group in Compounds (XI) is a t-butoxycarbonyl group, the reaction mixture resulting from the reaction of the step 10 is concentrated to dryness under reduced pressure and then treated in the same manner as in the step 7 in the presence of an acid.

Further, Compounds (I) can be synthesized using Compounds (X) as an intermediate as described below.

Compounds (X) are reacted with an acylating agent in an appropriate solvent as in the step 1. The obtained Compounds (VI) are treated in a similar manner as in the step 7 without or after isolation to eliminate the amino-protecting group, whereby Compounds (I) are obtained.

The practice of the present invention is illustrated by the following examples. The procedures in the examples were performed according to the respective steps as follows.

| Examples | Step |
|---|---|
| Examples 1, 2, 3, 7, 10, 16, 28 and 31 | step 1 |
| Examples 4 and 29 | step 2 |
| Examples 5, 6, 7, 11 and 25 | step 3 |
| Examples 11, 12, 13, 14, 15 and 26 | step 4 |
| Example 8 | step 5 |
| Examples 17, 18, 19, 20, 27 and 30 | steps 6 and 8 |
| Example 16 | step 7 |
| Example 9 | step 9 |
| Examples 21, 22, 23 and 24 | steps 10 and 11 |

EXAMPLE 1

Synthesis of 2'-N-t-butoxycarbonyl fortimicin B [the compound represented by the general formula (II) wherein R$_2$=(CH$_3$)$_3$COCO—]:

6.0 g of fortimicin B is dissolved in 300 ml of 50% (W/V) aqueous tetrahydrofuran solution and 5.8 g (1.4 moles per mole of the starting compound) of t-butyl-s-4,6-dimethylpyrimidine-2-ylthiocarbonate is added thereto. The mixture is allowed to stand at room temperature for 18 hours. Tetrahydrofuran is removed from the reaction mixture by distillation under reduced pressure. To the resulting solution is added 150 ml of water and the solution is adjusted to pH 5.5 with 1 N hydrochloric acid. The solution is passed through a column (2.5 cm in inside diameter) packed with 200 ml of a weakly acidic cation exchange resin, Amberlite CG-50 (NH$_4$$^+$ form) (Rohm & Haas Co., Ltd.). After the column is washed with 1 l of water, elution is carried out with 0.1 N aqueous ammonia. The eluate is taken in 20 g fractions. The fraction Nos. 22-44 are combined and concentrated under reduced pressure to obtain 2.86 g of a white powder. The powder has the following properties and is identified as 2'-N-t-butoxycarbonyl fortimicin B.

Yield: 37%

Rf value in silica gel thin layer chromatography [hereinafter referred to as TLC, plate: Fertigplatten Kieselgel 60 F 254 produced by E. Merck & Co., Inc. (the same plate is used in TLC hereinafter), developer:-lower layer of chloroform:methanol:14% aqueous ammonia=2:1:1 (by volume; the same shall apply hereinafter)]:0.63.

Nuclear magnetic resonance spectrum (in methanol-d$_4$) δ(ppm):1.07 (3H, d), 1.43 (9H, s), 2.41 (3H, s), 3.47 (3H, s), 4.98 (1H, s).

EXAMPLE 2

Synthesis of 2'-N-α-[(s)-β-benzyl-N-benzyloxycarbonylaspartyl] fortimicin B [the compound represented by the general formula (II) wherein

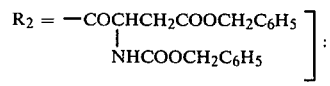

5.0 g (14.3 mmoles) of fortimicin B is dissolved in 140 ml of tetrahydrofuran: water (1:1) and 7.8 g (17.2 mmoles) of α-N-hydroxysuccinimide ester of (s)-β-benzyl-N-benzyloxycarbonyl aspartic acid is added thereto. The mixture is allowed to react at room temperature for 18 hours. Tetrahydrofuran is removed from the reaction mixture by distillation and to the resulting solution is added 70 ml of water. 140 ml of ethyl acetate is added thereto and the soluble part is removed by extraction. Water layer is adjusted to pH 10.5 with 1 N sodium hydroxide and twice extracted with 100 ml of chloroform. Chloroform layer is separated and dried over anhydrous sodium sulfate. The solvent is removed by distillation under reduced pressure to obtain 2.4 g of a white powder. The powder has the following properties and is identified as the above-indicated compound. Yield: 24.3%.

Rf value in silica gel TLC (developer:lower layer of chloroform:methanol:14% aqueous ammonia=2:1:1):0.52.

Nuclear magnetic resonance spectrum (in methanol-d4) δ(ppm):1.03 (3 H, d), 2.36 (3H, s), 2.6~3.1 (5H, m), 3.44 (3H, s), 5.01 (1H, d), 5.12 (4H, s), 7.33 (10H, s).

EXAMPLE 3

Synthesis of 2'-N-α-[(s)-N-benzyloxycarbonylasparaginyl]fortimicin B [the compound represented by the general formula (II) wherein

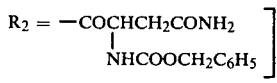

1.5 g of 2'-N-α-[(s)-β-benzyl-N-benzyloxycarbonyl aspartyl9 fortimicin B obtained in Example 2 is dissolved in 30 ml of methanol saturated with ammonia gas and the mixture is allowed to stand at room temperature for 24 hours. After the reaction mixture is concentrated, 30 ml of water is added to the residue. The aqueous solution is adjusted to pH 6 with 1 N hydrochloric acid. The solution is passed through a column (1.8 cm in inside diameter) packed with 50 ml of a weakly acidic cation exchange resin, Amberlite CG-50 ($NH_4^+$ form). After the column is washed with 300 ml of water, elution is carried out with 0.1 N aqueous ammonia. The eluate is taken in 20 ml fractions. The fraction Nos. 16–28 are combined and aqueous ammonia is removed therefrom by distillation to obtain 1.02 g of a white powder. The powder has the following properties and is identified as 2'-N-α-[(s)-N-benzyloxycabonyl asparaginyl] fortimicin B. Yield: 78.2%.

Rf value in silica gel TLC (developer:lower layer of chloroform:methanol:14% aqueous ammonia=2:1:1):0.48.

Nuclear magnetic resonance spectrum (in methanol-d4) δ(ppm):1.04 (3H, d), 2,34 (3H, s), 2.4~2.9 (4H, m), 3.44 (3H, s), 4.92 (1H, d), 5.12 (2H, s), 7.33 (5H, s).

EXAMPLE 4

Synthesis of 2'-N-t-butoxycarbonyl-1,6'-di-N-benzyloxycarbonyl fortimicin B [the compound represented by the general formula (III) wherein $R_2$=(CH$_3$)$_3$COCO and $R_4$=COOCH$_2$C$_6$H$_5$]:

2.0 g of 2'-N-t-butoxycarbonyl fortimicin B obtained in Example 1 is dissolved in 120 ml of methanol and 2.44 g (2.2 moles per mole of the starting compound) of N-benzyloxycarbonyloxysuccinimide is added thereto. The mixture is allowed to react at room temperature for 3 hours and methanol is removed from the reaction mixture by distillation under reduced pressure. To the residue is added 120 ml of ethyl acetate and the solution is washed with 120 ml of water. After ethyl acetate layer is dried over anhydrous sodium sulfate, the solvent is removed by distillation under reduced pressure to obtain a crude powder of the desired substance. For purification, the crude powder is dissolved in 10 ml of chloroform and the solution is passed through a column (2.5 cm in inside diameter) packed with 80 g of silica gel (Kieselgel 60 produced by E. Merck & Co., Inc., hereinafter the same silica gel is used for column chromatography). Elution is carried out with chloroform:methanol (24:1). The eluate is taken in 20 ml fractions. The fraction Nos. 19–60 are combined and the solvent is removed therefrom by distillation to obtain 2.42 g of a white powder. The powder has the following properties and is identified as 2'-N-t-butoxycarbonyl-1,6'-di-N-benzyloxycarbonyl fortimicin B. Yield: 75.7%.

Rf value in silica gel TLC (developer:chloroform:methanol=9:1):0.52.

Nuclear magnetic resonance spectrum (in methanol-d4) δ(ppm):1.02 (3H, d), 1.40 (9H, s), 2.37 (3H, s), 3.47 (3H, s), 5,03 (4H, s), 5.31 (1H, d), 7.30 (10H, s).

EXAMPLE 5

Synthesis of 2'-N-[(s)-2-amino-4-hydroxybutyl] fortimicin B [the compound represented by the general formula (IV) wherein $R_0$=H and

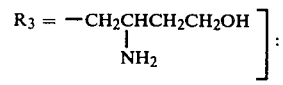

830 mg (1.2 mmoles) of 2'-N-α-[(s)-β-benzyl-N-benzyloxycarbonylaspartyl] fortimicin B obtained in Example 2 is dissolved in 10 ml of tetrahydrofuran and 12 ml of a diborane solution in tetrahydrofuran (1 mole solution of BH$_3$) is added thereto. The mixture is allowed to react at room temperature for 1 hour. To the reaction mixture is added 0.4 ml of water to decompose the excess diborane. The solution is concentrated to dryness and to the residue are added 22 ml of 0.2 N-hydrochloric acid methanol* and 100 mg of 10% palladium carbon catalyst. Hydrogen gas is bubbled through the solution and hydrogenolysis is carried out at room temperature and at atmospheric pressure for 18 hours. The catalyst is filtered off from the reaction mixture. The filtrate is concentrated and to the residue is added 30 ml of water. The solution is adjusted to pH 6 with 1 N sodium hydroxide. The resulting solution is passed through a column (1.5 cm in inside diameter) packed with 50 ml of Amberlite CG-50 ($NH_4^+$ form) to adsorb the desired substance on the resin. The column is washed with 300 ml of water. Elution is carried out with 0.2 N aqueous ammonia. The eluate is taken in 15 ml fractions. The fraction Nos. 12–39 are combined and aqueous ammonia is evaporated to dryness to obtain 340 mg of a white powder. The powder has the following properties and is identified as the above-indicated compound. Yield: 64.3%.

* prepared by diluting 12 N hydrochloric acid with methanol. (The same shall apply hereinafter).

Rf value in silica gel TLC (developer:lower layer of chloroform:methanol:28% aqueous ammonia=1:1:1):0.59.

Nuclear magnetic resonance spectrum (in methanol-d4) δ(ppm):1.08 (3H, d), 1.3–2.0 (6H, m), 2.37 (3H, s), 2.4–3.1 (7H, m), 3.43 (3H, s), 5.13 (1H, d).

Mass spectrum (m/e) 436(M+), 361, 346, 332, 230, 207, 155, 126.

EXAMPLE 6

Synthesis of 2'-N-[(s)-2,4-diaminobutyl] fortimicin B [the compound represented by the general formula (IV) wherein $R_0$=H and

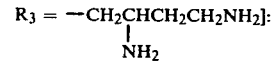

The same procedure as in Example 5 is repeated except that 720 mg (1.2 mmoles) of 2'-N-α-[(s)-N-benzyloxycarbonylasparaginyl] fortimicin B obtained in Example 3 is used instead of 2'-N-α-[(s)-β-benzyl-N-benzyloxycarbonylaspartyl] fortimicin B. From the fraction Nos. 20–38, 350 mg of a white powder having the following properties is obtained. The powder is identified as the above-indicated compound. Yield: 67.2%.

Rf value in silica gel TLC (developer:lower layer of chloroform:methanol:28% aqueous ammonia=1:1:1):0.37

Nuclear magnetic resonance spectrum (in methanol-$d_4$) $\delta$(ppm):1.08 (3H, d), 1.2–1.9 (6H, m), 2.36 (3H, s), 2.4–3.1 (9H, m), 3.43 (3H, s), 5.16 (1H, d).

Mass spectrum (m/e) 435(M+), 404, 387, 361, 332, 247, 235, 229, 207, 155, 104.

EXAMPLE 7

Synthesis of 2'-N-[(s)-2-amino-3-benzyloxypropyl] fortimicin B [the compound represented by the general formula (IV) wherein $R_0$=H and

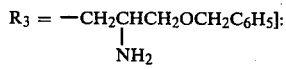

1.4 g of (s)-N-t-butoxycarbonyl-o-benzylserine and 0.6 g of N-hydroxysuccinimide are dissolved in 25 ml of tetrahydrofuran and 1.1 g of dicyclohexylcarbodiimide is added thereto under ice cooling. The mixture is stirred at the same temperature for 1 hour. The precipitated crystal is removed by filtration and the filtrate is added to 25 ml of methanol in which 1.6 g of fortimicin B is dissolved. The mixture is allowed to stand at room temperature for 18 hours. The reaction mixture is concentrated to dryness. To the residue are added 50 ml of water and 50 ml of chloroform and the mixture is vigorously stirred. Chloroform layer is dried over anhydrous sodium sulfate and the solution is evaporated to dryness to obtain a pale yellowish powder containing the desired substance. The powder is dissolved in 20 ml of tetrahydrofuran and 15 ml of diborane solution in tetrahydrofuran (1 mole solution of $BH_3$) is added thereto. The mixture is allowed to react at room temperature for 1 hour. To the reaction mixture is added 0.5 ml of water to decompose unreacted diborane and the solution is concentrated to dryness. After the residue is well dried, 10 ml of trifluoroacetic acid is added thereto and the mixture is allowed to stand at room temperature for 1 hour. After the reaction mixture is concentrated, 50 ml of water is added thereto. The aqueous solution is adjusted to pH 6 with 1 N sodium hydroxide. The solution is passed through a column (1.5 cm in inside diameter) packed with 50 ml of Amberlite CG-50 ($NH_4^+$ form). After the column is washed with 300 ml of water, elution is carried out with 0.15 N aqueous ammonia. The eluate is taken in 15 ml fractions. The fraction Nos. 6–24 are combined and aqueous ammonia is removed therefrom by distillation to obtain 850 mg of a white powder. The powder has the following properties and is identified as the above-indicated compound. Yield: 38.6%

Rf value in silica gel TLC (developer:lower layer of chloroform:methanol:14% aqueous ammonia=2:1:1):0.40.

Nuclear magnetic resonance spectrum (in methanol-$d_4$) $\delta$(ppm): 1.06 (3H, d), 2.6–3.1 (7H, m), 2.34 (3H, s), 3.41 (3H, s), 3.92 (2H, s), 4.92 (1H, d), 7.35 (5H, s).

Mass spectrum (m/e) 512(M+), 431, 403, 361, 332, 306, 235, 207, 155, 91.

EXAMPLE 8

Synthesis of 2'-N-t-butoxycarbonyl-1,6'-di-N-benzyloxycarbonyl-4-N-(N-benzloxycarbonylglycyl) fortimicin B [the compound represented by the general formula (VI) wherein $R_2$=$(CH_3)_3COCO$— and $R_4$=$C_6H_5CH_2OCO$—]

800 mg of N-benzyloxycarbonylglycine and 540 mg of 1-hydroxybenzotriazole are dissolved in 80 ml of tetrahydrofuran and 890 mg of N,N'-dicyclohexylcarbodiimide is added thereto. The mixture is stirred under ice cooling (0°–5° C.) for 1 hour to synthesize 1-hydroxybenzotriazole ester of N-benzyloxycarbonylglycine. To the mixture is added 2.40 g of 2'-N-t-butoxycarbonyl-1,6'-di-N-benzyloxycarbonyl fortimicin B obtained in Example 4 and the resulting mixture is stirred at room temperature for 18 hours. The precipitated insoluble matters are removed by filtration. The filtrate is concentrated to dryness under reduced pressure to obtain a pale yellowish crude powder of the desired substance. For purification, the residue is dissolved in 10 ml of chloroform and the solution is passed through a column (2 cm in inside diameter) packed with 80 g of silica gel. Elution is carried out with methanol:chloroform (1:49). The eluate is taken in 16 ml fractions. The fraction Nos. 11–32 are combined and concentrated to dryness to obtain 2.69 g of a white powder. The powder has the following properties and is identified as the above-indicated compound. Yield: 88.5%.

Rf value in silica gel TLC (developer:chloroform:methanol=19:1):0.40

Nuclear magnetic resonance spectrum (in methanol-$d_4$); $\delta$(ppm): 1.13 (3H, d), 1.35 (9H, s), 3.07 (3H, s), 3.35 (3H, s), 4.06 (2H, s), 5.03 (2H, s), 5.07 (4H, s), 7.29 (15H, s).

EXAMPLE 9

Synthesis of 1,6'-di-N-benzyloxycarbonyl-4-N-(N-benzyloxycarbonylglycyl) fortimicin B [the compound represented by the general formula (X) wherein $R_4$=$COOCH_2C_6H_5$]

2.53 g of 2'-N-t-butoxycarbonyl-1,6'-di-N-benzyloxycarbonyl-4-N-(N-benzyloxycarbonylglycyl) fortimicin B obtained in Example 8 is dissolved in 20 ml of chloroform and 10 ml of trifluoroacetic acid (about 20 moles per mole of the starting compound) is added thereto. The mixture is allowed to react at room temperature for 1 hour. After the reaction mixture is concentrated under reduced pressure, 150 ml of ethyl acetate is added thereto. The resulting solution is washed with water and aqueous saturated solution of sodium hydrogencarbonate. After ethyl acetate layer is dried over anhydrous sodium sulfate, the solvent is removed by distillation under reduced pressure to obtain 1.93 g of a white powder. The powder has the following properties and is identified as the above-indicated compound.

Rf value in silica gel TLC (developer:chloroform:methanol=9:1):0.18.

Nuclear magnetic resonance spectrum (in methanol-$d_4$) $\delta$(ppm): 1.13 (3H, d), 3.07 (3H, s), 3.36 (3H, s), 4.89 (1H, d), 5.05 (2H, s), 5.09 (4H, s), 7.30 (15H, s).

EXAMPLE 10

Synthesis of 2'-N-(N-t-butoxycarbonylglycyl) fortimicin B [the compound represented by the general formula (II) wherein $R_2=COCH_2NHCOOC(CH_3)_3$]:

The same procedure as in Example 1 is repeated except that 6.56 g (1.4 moles per mole of the starting compound) of N-hydroxysuccinimide ester of N-t-butoxycarbonylglycine is used instead of 5.8 g of t-butyl-s-4,6-dimethylpyrimidine-2-ylthiocarbonate. From the fraction Nos. 38–54, 3.18 g of a white powder having the following properties is obtained. The powder has the following properties and is identified as the above-indicated compound. Yield: 36.5%.

Rf value in silica gel TLC (developer:lower layer of chloroform:methanol:14% aqueous ammonia=2:1:1):0.39.

Nuclear magnetic resonance spectrum (in methanol-$d_4$); $\delta$(ppm): 1.08 (3H, d), 1.44 (9H, s), 2.43 (3H, s), 3.45 (3H, s), 4.06 (2H, s), 4.98 (1H, d).

EXAMPLE 11

Synthesis of 2'-N-(2-aminoethyl)-1,6'-di-N-benzyloxycarbonyl fortimicin B [the compound represented by the general formula (V) wherein $R_0=H$, $R_3=-CH_2CH_2NH_2$ and $R_4=-COOCH_2C_6H_5$]

2.02 g (4 mmoles) of 2'-N-(N-t-butoxycarbonylglycyl) fortimicin B obtained in Example 10 is dissolved in 40 ml of tetrahydrofuran and 40 ml of a diborane solution in tetrahydrofuran (1 mole solution of $BH_3$) is added thereto. The mixture is allowed to react at room temperature for 1 hour. To the reaction mixture is added 1 ml of water to decompose unreacted diborane and the mixture is concentrated to dryness. To the residue is added 50 ml of 0.2 N hydrochloric acid and the mixture is allowed to stand overnight. Then the mixture is adjusted to pH 10 with 1 N NaOH. To the mixture are added 100 ml of tetrahydrofuran and 2.2 g of N-benzyloxycarbonyloxysuccinimide (8.8 mmoles). The mixture is allowed to react at room temperature for 16 hours. From the reaction mixture tetrahydrofuran is removed by distillation. To the resulting solution is added 100 ml of ethyl acetate to extract soluble matters. After ethyl acetate layer is washed with 100 ml of water, the layer is separated and dried over anhydrous sodium sulfate. The solvent is removed by distillation therefrom to obtain a pale yellowish powder. The powder is dissolved in 15 ml of chloroform and 10 ml of trifluoroacetic acid is added thereto. The mixture is allowed to react at room temperature for 1 hour. The reaction mixture is concentrated and 100 ml of water is added thereto. The aqueous solution is adjusted to pH 10 with 1 N sodium hydroxide and extracted twice with 100 ml of chloroform. Chloroform layer is separated and the solvent is removed therefrom by distillation to obtain 1.54 g of a pale yellowish powder. The powder has the following properties and is identified as the above-indicated compound. Yield: 58.4%.

Rf value in silica gel TLC (developer:lower layer of methanol:chloroform:14% aqueous ammonia = 1:2:1):0.61.

Nuclear magnetic resonance spectrum (in methanol-$d_4$); $\delta$(ppm): 1.03 (3H, d), 2.37 (3H, s), 2.67 (4H, s), ~3.0 (2H, m), 3.47 (3H, s), 5.02 (4H, s), 5.18 (H, d).

EXAMPLE 12

Synthesis of 2'-N-[(s)-2-benzyloxycarbonylamino-4-hydroxybutyl]-1,6'-di-N-benzyloxycarbonyl fortimicin B [the compound represented by the general formula (V) wherein $R_0=H$, $R_3 = -CH_2\overset{\overset{\displaystyle NHCOOCH_2C_6H_5}{|}}{C}HCH_2CH_2OH$ and $R_4 = COOCH_2C_6H_5$]:

440 mg (1.0 mmole) of 2'-N-[(s)-2-amino-4-hydroxybutyl] fortimicin B obtained in Example 5 is dissolved in 20 ml of methanol and 820 mg (3.3 mmoles) of N-benyloxycarbonyloxysuccinimide is added thereto. The mixture is allowed to react at room temperature for 18 hours. The reaction mixture is concentrated and to the residue is added 5 ml of chloroform to extract soluble matters. The chloroform solution is passed through a column (1.5 cm in inside diameter) packed with 25 g of silica gel. Elution is carried out with chloroform:methanol = 19:1 and the eluate is taken in 20 ml fractions. The fraction Nos. 16–28 are combined and the solvent is removed therefrom by distillation to obtain 640 mg of a white powder. The powder has the following properties and is identified as the above-indicated compound. Yield: 76.4%.

Rf value in silica gel TLC (developer:chloroform:methanol = 9:1):0.27.

Nuclear magnetic resonance spectrum (in methanol-$d_4$); $\delta$(ppm): 1.02 (3H, d), 1.1–1.8 (6H, m), 2.37 (3H, s), 2.4–3.1 (4H, m), 3.46 (3H, s), 5.02 (2H, s), 5.08 (4H, s), 7.33 (15H, s).

EXAMPLE 13

Synthesis of 2'-N-[(s)-2,4-di-benzyloxycarbonylaminobutyl]-1,6'-di-N-benzyloxycarbonyl fortimicin B [the compound represented by the general formula (V) wherein $R_0=H$, $R_3 = -CH_2\overset{\overset{\displaystyle NHCOOCH_2C_6H_5}{|}}{C}HCH_2CH_2NHCOOCH_2C_6H_5$ and $R_4 = -COOCH_2C_6H_5$]:

The same procedure as in Example 12 is repeated except that 430 mg (1.0 mmole) of 2'-N-[(s)-2,4-diaminobutyl] fortimicin B obtained in the same manner as in Example 6 is used instead of 2'-N-[(s)-2-amino-4-hydroxybutyl] fortimicin B and that 1.1 g (4.4 mmoles) of N-benzyloxycarbonyloxysuccinimide is used. The obtained powder (660 mg) has the following properties and is identified as the above-indicated compound. Yield: 68.3%.

Rf value in silica gel TLC (developer:chloroform:methanol = 9:1):0.39.

Nuclear magnetic resonance spectrum (in methanol-$d_4$), $\delta$(ppm): 1.04 (3H, d), 1.1–1.8 (6H, m), 2.36 (3H, s), 3.46 (3H, s), 5.06 (8H, s), 7.35 (20H, s).

EXAMPLE 14

Synthesis of 2'-N-[(s)-2-benzyloxycarbonylamino-3-benzyloxypropyl]-1,6'-di-N-benzyloxycarbonyl fortimicin B [the compound represented by the general formula (V) wherein $R_0=H$,

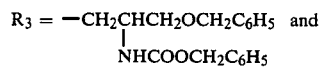

The same procedure as in Example 12 is repeated except that 510 mg (1 mmole) of 2-N-[(s)-2-amino-3-benzyloxypropyl] fortimicin B prepared in Example 7 is used instead of 2'-N-[(s)-2-amino-4-hydroxybutyl] fortimicine B. The obtained white powder (730 mg) has the following properties and is identified as the above-indicated compound. Yield: 80.1%.

Rf value in silica gel TLC (developer:chloroform:methanol=17:3):0.48.

NMR spectrum (in methanol-d4) δ(ppm): 1.06 (3H, s), 2.38 (3H, s), 2.8–3.2 (3H, m), 3.43 (3H, s), 3.92 (2H, s), 5.02 (4H, s), 7.33 (15H, s).

EXAMPLE 15

Synthesis of 2'-N-(2-nitroguanidinoethyl)-1,6'-di-N-benzyloxycarbonyl fortimicin B [the compound represented by the general formula (V) wherein $R_0=H$,

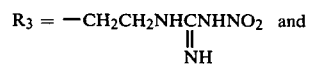

800 mg (1.2 mmoles) of 2'-N-(2-aminoethyl)-1,6'-di-N-benzyloxycarbonyl fortimicin B prepared in the same manner as in Example 11 is dissolved in 20 ml of methanol. To the solution is added 240 mg of 1-nitroguanidyl-3,5-dimethylpyrazol. The mixture is allowed to react at room temperature for 3 hours. The reaction mixture is concentrated and the residue is dissolved in 5 ml of chloroform. The solution is passed through a column (1.5 cm in inside diameter) packed with 25 g of silica gel to adsorb the desired substance on the silica gel. Elution is carried out with chloroform:methanol=9:1 and the eluate is taken in 20 ml fractions. The fraction Nos. 12–40 are combined and the solvent is removed therefrom by distillation to obtain 620 mg of a white powder. The powder has the following properties and is identified as the above-indicated compound. Yield: 68%.

Rf value in silica gel TLC (developer:chloroform:methanol=4:1):0.31.

Nuclear magnetic resonance spectrum (in methanol-d4), δ(ppm): 1.02 (3H, s), 2.37 (3H, s), 2.7–3.1 (3H, m), 3.45 (3H, s), 5.03 (4H, s), 5.18 (1H, d), 7.34 (10H, s).

EXAMPLE 16

Synthesis of 2'-N-hydantoyl fortimicin A (Compound 2) [the compound represented by the general formula (I) wherein $R_0=H$ and $R=-COCH_2NHCONH_2$]:

200 mg (0.85 mmole) of hydantoic acid and 75 mg (0.84 mmole) of N-hydroxysuccinimide are dissolved in 8 ml of tetrahydrofuran. 180 mg of N,N'-di-cyclohexylcarbodiimide is added thereto under ice cooling. The mixture is stirred for 1 hour. The precipitated crystal is removed by filtration and to the filtrate is added 500 mg of 1,6'-di-N-benzyloxycarbonyl-4-N-(N-benzyloxycarbonylglycyl) fortimicin B prepared in Example 9. The mixture is allowed to react at room temperature for 6 hours. The reaction mixture is concentrated and to the residue are added 15 ml of 0.2 N-hydrochloric acid methanol and 50 mg of palladium carbon catalyst. Hydrogen gas is bubbled through the solution and reductive hydrogenolysis is carried out for 3 hours. From the reaction mixture the catalyst is filtered off and the filtrate is concentrated. To the residue is added 15 ml of water. The solution is adjusted to pH 6 with 1 N sodium hydroxide. The solution is passed through a column (0.8 cm in inside diameter) packed with 30 ml of Amberlite CG-50 ($NH_4^+$ form) to adsorb the desired substance on the resin. The column is washed with 150 ml of water. Then, elution is carried out with 0.2 N aqueous ammonia and the eluate is taken in 15 ml fractions. The fraction Nos. 12–16 are combined and aqueous ammonia is removed therefrom by distillation to obtain 240 mg of a white powder. The powder has the following properties and is identified as the above-indicated compound. Yield: 83.4%.

Rf value in silica gel TLC (developer:lower layer of chloroform:methanol:28% aqueous ammonia=1:1:1):0.41.

Nuclear magnetic resonance spectrum (in heavy water) δ(ppm):1.07 (3H, d), 1.2–1.8 (4H, m), 3.06 (3H, s), 3.45 (3H, s), 3.53 (2H, s), 4.91 (1H, d), 3.84 (2H, s).

Specific rotation (sulfate): $[\alpha]_D^{23}=+103.0°$ (C=0.2, $H_2O$).

EXAMPLE 17

Synthesis of 2'-N-[(s)-2-amino-4-hydroxybutyl] fortimicin A (Compound 5) [the compound represented by the general formula (I) wherein $R_0=H$ and

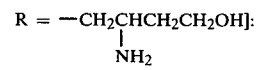

160 mg of N-benzyloxycarbonylglycine and 110 mg of 1-hydroxybenzotriazole are dissolved in 20 ml of tetrahydrofuran. To the solution is added 180 mg of N,N'-di-cyclohexylcarbodiimide under ice cooling. The mixture is allowed to react at 0°–5° C. for 1 hour. The precipitated crystal is removed from the reaction mixture by filtration and to the filtrate is added 590 mg (0.7 mmole) of 2'-N-[(s)-2-benzyloxycarbonylamino-4-hydroxybutyl]-1,6'-di-N-benzyloxycarbonyl fortimicin B obtained in Example 12. The mixture is allowed to react at room temperature for 18 hours. The reaction mixture is concentrated to dryness and to the residue are added 20 ml of 0.2 N hydrochloric acid methanol and 70 mg of palladium carbon catalyst. Hydrogen gas is bubbled through the solution and reductive hydrogenolysis is carried out for 6 hours. The catalyst is filtered off from the reaction mixture.

After the filtrate is concentrated, 20 ml of water is added thereto. The aqueous solution is adjusted to pH 6 with 1 N sodium hydroxide. The solution is passed through a column (0.8 cm in inside diameter) packed with 30 ml of Amberlite CG-50 ($NH_4^+$ form). The column is washed with 150 ml of water. Then, elution is carried out with 0.4 N aqueous ammonia. The eluate is taken in 15 ml fractions. The fraction Nos. 21–29 are combined. The solvent is removed therefrom by distillation to obtain 110 mg of a white powder. The powder has the following properties and is identified as the above-indicated compound. Yield: 31.7%.

Rf value in silica gel TLC (developer:lower layer of chloroform:methanol:28% aqueous ammonia=1:1:1):0.54.

Nuclear magnetic resonance spectrum (in heavy water) δ(ppm): 1.11 (3H, d), 16–1.9 (6H, m), 3.05 (3H, s), 3.44 (3H, s), 3.54 (2H, s), 4.98 (1H, d).

Specific rotation (free base): $[\alpha]_D^{21} = +84.5°$ (C=0.2, H$_2$O).

Mass spectrum: 492(M+), 418, 400, 361, 332, 247, 230, 207, 155.

EXAMPLE 18

Synthesis of 2'-N-(2,4-diaminobutyl) fortimicin A (Compound 6) [the compound represented by the general formula (I) wherein R$_0$=H and

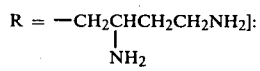

The same procedure as in Example 17 is repeated except that 680 mg (0.7 mmole) of 2'-N-(2,4-di-benzyloxycarbonylaminobutyl)-1,6'-di-N-benzyloxycarbonyl fortimicin B obtained in Example 13 is used instead of 2'-N-[(s)-2-benzyloxycarbonylamino-4-hydroxybutyl]-1,6'-di-N-benzyloxycarbonyl fortimicin B. The obtained white powder (210 mg) has the following properties and is identified as the above-indicated compound. Yield: 61%.

Rf value in silica gel TLC (The same developer as in Example 17 is used.): 0.35.

Nuclear magnetic resonance spectrum (in heavy water) δ(ppm): 1.04 (3H, d), 1.2–2.0 (6H, m), 2.3–3.0 (7H, m), 3.06 (3H, s), 3.44 (3H, s), 3.52 (2H, s), 5.06 (1H, d).

Specific rotation (sulfate): $[\alpha]_D^{21} = +55.5°$ (C=0.2, H$_2$O).

Mass spectrum (m/e): 491(M+), 474, 473, 435, 387, 361, 246, 229, 207, 155, 104.

EXAMPLE 19

Synthesis of 2'-N-[(s)-2-amino-3-hydroxypropyl]fortimicin A (Compound 7) [the compound represented by the general formula (I) wherein R$_0$=H and

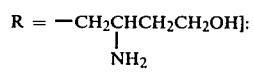

The same procedure as in Example 17 is repeated except that 640 mg (0.7 mmole) of 2'-N-[(s)-2-benzyloxycarbonylamino-3-benzyloxypropyl]-1,6'-di-N-benzyloxycarbonyl fortimicin B obtained in Example 14 is used instead of 2'-N-[(s)-2-benzyloxycarbonylamino-4-hydroxybutyl]-1,6'-di-N-benzyloxycarbonyl fortimicin B. The obtained white powder (230 mg) has the following properties and is identified as the above-indicated compound. Yield: 68.6%.

Rf value in silica gel TLC (The same developer as in Example 17 is used): 0.50.

Nuclear magnetic resonance spectrum (in heavy water), δ(ppm): 1.05 (3H, d), 2.6–3.0 (6H, m), 3.05 (3H, s), 3.44 (3H, s), 3.52 (2H, s), 5.07 (1H, d).

Specific rotation (sulfate): $[\alpha]_D^{21} = +57.5°$ (C=0.2, H$_2$O).

EXAMPLE 20

Synthesis of 2'-N-(2-guanidinoethyl) fortimicin A (Compound 10) [the compound represented by the general formula (I) wherein R$_0$=H and

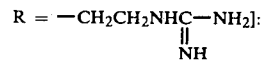

180 mg of N-benzyloxycarbonylglycine and 120 mg of 1-hydroxybenzotriazole are dissolved in 22 ml of tetrahydrofuran. 180 mg of N,N'-di-cyclohexylcarbodiimide is added to the solution under ice cooling. The mixture is allowed to react at 0°–5° C. for 1 hour. The precipitated crystal is removed by filtration and to the filtrate is added 590 mg of 2'-N-(2-nitroguanidinoethyl)-1,6'-di-N-benzyloxycarbonyl fortimicin B (obtained in Example 15). The mixture is allowed to react at room temperature for 18 hours. The reaction mixture is concentrated and to the residue is added 5 ml of chloroform. The solution is passed through a column (1.5 cm in inside diameter) packed with 25 g of silica gel. Elution is carried out with chloroform:methanol=47:3. The eluate is taken in 15 ml fractions. The fraction Nos. 45–69 are combined. The solvent is removed therefrom by distillation to obtain 660 mg of a white powder.

Rf value in silica gel TLC:0.32 (developer:-chloroform-methanol=9:1)

610 mg of the powder is dissolved in 20 ml of methanol. To the solution are added 3.9 ml of 1 N sulfuric acid and 60 mg of palladium carbon catalyst. Reductive hydrogenolysis is carried out for 18 hours while blowing hydrogen gas through the reaction mixture. The catalyst is filtered off. The filtrate is concentrated to 0.5 ml and is added to 100 ml of ethanol by portions to obtain a precipitate. The precipitate is isolated by filtration and dried to obtain 280 mg of a white powder. The powder has the following properties and is identified as a sulfuric acid addition salt of the above-indicated compound.

Yield: 52%.

Rf value in silica gel TLC (a) developer:isopropanol:chloroform:28% aqueous ammonia=2:1:1:0.16.

(b) developer:lower layer of chloroform:methanol:28% aqueous ammonia=1:1:1:0.14.

Nuclear magnetic resonance spectrum (in heavy water) p0=2.0; δ(ppm): 1.35 (3H, d), 3.14 (3H, s), 3.49 (3H, s), 4.10 (2H, s), 5.42 (1H, H).

Specific rotation (sulfate):$[\alpha]_D^{21.5} = +48.5°$ (C=0.2, H$_2$O).

Sakaguchi reaction:positive.

EXAMPLE 21

Synthesis of 2'-N-amidino fortimicin A (Compound 4) [the compound represented by the general formula (I) wherein R$_0$=H and

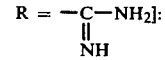

500 mg of 1,6'-di-N-benzyloxycarbonyl-4-N-(N-benzyloxycarbonylglycyl) fortimicin B obtained in Example 9 is dissolved in 12 ml of methanol. To the solution is added 120 mg of 1-nitroguanidyl-3,5-dimethylpyrazol. The mixture is allowed to react at room temperature for 18 hours. The reaction mixture is concentrated and to the residue is added 4 ml of chloroform to extract soluble matters. The chloroform solution is passed through a column (1.5 cm in inside diameter) packed with 20 g of silica gel. Elution is carried out with chloroform:methanol=24:1. The eluate is taken in 10 ml fractions. The fraction Nos. 10–28 are combined and the solvent is removed by distillation to obtain 260 mg of a white powder. (Rf value in silica gel TLC using chloroform:methanol=9:1 as a developer:0.67) The powder is dissolved in 20 ml of methanol. To the solution are added 1.45 ml of 1 N sulfuric acid and 50 mg of palladium carbon catalyst. Reductive hydrogenolysis is carried out for 18 hours while blowing hydrogen gas through the reaction mixture. The catalyst is filtered off from the reaction mixture. The filtrate is concentrated to 0.5 ml and is dropwise added to 80 ml of ethanol with stirring. The resulting precipitate is isolated by filtration and dried to obtain 160 mg of a white powder. The powder has the following properties and is identified as a sulfuric acid addition salt of the above-indicated compound. Yield: 33%.

Rf value in silica gel TLC
(a) developer:lower layer of chloroform:methanol:28% aqueous ammonia=1:1:1:0.13.
(b) developer:isopropanol:chloroform:28% aqueous ammonia=2:1:1:0.26.

Nuclear magnetic resonance spectrum (in heavy water) pD=1.5, δ(ppm): 1.34 (3H, d), 3.12 (3H, s), 3.49 (3H, s), 4.08 (2H, s), 5.39 (1H, d).

Sakaguchi reaction:positive.

Specific rotation (sulfate):$[\alpha]_D^{21.5} = +65.0°$ (C=0.2, H$_2$O).

EXAMPLE 22

Synthesis of 2′-N-(2,3-dihydroxypropyl) fortimicin A (Compound 8) [the compound represented by the general formula (I) wherein R$_0$=H and

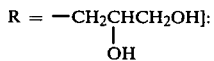

500 mg of 1,6′-di-N-benzyloxycarbonyl-4-N-(N-benzyloxycarbonylglycyl) fortimicin B obtained in Example 9 is dissolved in 15 ml of methanol. To the solution are added 220 mg of D,L-glyceroaldehyde and 120 mg of sodium boron hydride. The mixture is stirred at room temperature for 3 hours. To the reaction mixture are added 5 ml of 1 N hydrochloric acid and 50 mg of palladium carbon catalyst. Reductive hydrogenolysis is carried out for 4 hours while blowing hydrogen gas through the reaction mixture. The catalyst is filtered off from the reaction mixture. The filtrate is concentrated and 20 ml of water is added thereto. The aqueous solution is adjusted to pH 6 with 1 N sodium hydroxide. The solution is passed through a column (0.8 cm in inside diameter) packed with 30 ml of Amberlite CG-50 (NH$_4$+ form). The column is washed with 150 ml of water. Then, elution is carried out with 0.2 N aqeuous ammonia. The eluate is taken in 15 ml fractions. The fraction Nos. 18–21 are combined and aqueous ammonia is removed therefrom by distillation to obtain 110 mg of a white powder. The powder has the following properties and is identified as the above-indicated compound. Yield: 37.1%

Rf value in silica gel TLC (developer:lower layer of chloroform: 28% aqueous ammonia:methanol=1:1:1):0.52.

Nuclear magnetic resonance spectrum (in heavy water), δ(ppm): 1.08 (3H, d), 2.6–3.1 (5H, m), 3.05 (3H, s), 3.44 (3H, s), 3.53 (2H, s), 4.98 (1H, d).

Specific rotation (sulfate): $[\alpha]_D^{21.5} = +70.0°$ (C=0.2, H$_2$O).

Mass spectrum (m/e) 479 (M+), 461, 404, 366, 332, 235, 207, 190, 174, 142, 117.

EXAMPLE 23

Synthesis of 2′-N-2-(1,3-dihydroxypropyl) fortimicin A (Compound 9) [the compound represented by the general formula (I) wherein R$_0$=H and R=—CH(CH$_2$OH)$_2$]:

The same procedure as in Example 22 is repeated except that 220 mg of dihydroxyacetone is used instead of D,L-glyceroaldehyde. The obtained powder (130 mg) has the following properties and is identified as the above-indicated compound. Yield: 44%.

Rf value in silica gel TLC (The same developer as in Example 22 is used): 0.48.

Nuclear magnetic resonance spectrum (in heavy water), δ(ppm): 1.04 (3H, s), 3.05 (3H, s), 3.45 (3H, s), 3.53 (2H, s), 3.61 (4H, d), 5.01 (1H, d).

Specific rotation (sulfate): $[\alpha]_D^{21.5} = +67.5°$ (C=0.2, H$_2$O).

EXAMPLE 24

Synthesis of 2′-N-carbamoyl fortimicin A (Compound 3) [the compound represented by the general formula (I) wherein R$_0$=H and R=—CONH$_2$]:

500 mg of 1,6′-di-N-benzyloxycarbonyl-4-N-(N-benzyloxycarbonylglycyl) fortimicin B obtained in Example 9 is dissolved in a mixture of 10 ml of acetic acid and 3 ml of water. To the solution is dropwise added 200 mg of potassium cyanate dissolved in 2 ml of water. The mixture is allowed to react at room temperature for 6 hours. After the reaction mixture is concentrated, 20 ml of ethyl acetate is added thereto to extract soluble matters. The ethyl acetate solution is concentrated and to the residue are added 20 ml of 0.2 N hydrochloric acid methanol and 50 ml of palladium carbon catalyst. Reductive hydrogenolysis is carried out for 8 hours while blowing hydrogen gas through the mixture. The catalyst is filtered off from the reaction mixture. The filtrate is concentrated and to the residue is added 20 ml of water. The aqueous solution is adjusted to pH 6 with 1 N sodium hydroxide. The solution is passed through a column (0.8 cm in inside diameter) packed with 30 ml of Amberlite CG-50 (NH$_4$+ form). The column is washed with 150 ml of water. Elution is carried out with 0.2 N aqueous ammonia. The eluate is taken in 15 ml fractions. The fraction Nos. 8–16 are combined and ammonia is removed therefrom by distillation to obtain 140 mg of a white powder. The powder has the following properties and is identified as the above-indicated compound. Yield: 50%.

Rf value in silica gel TLC (The same developer as in Example 22 is used): 0.56.

Nuclear magnetic resonance spectrum (in heavy water) δ(ppm): 1.04 (3H, d), 2.7–3.0 (2H, m), 3.06 (3H, s), 3.44 (3H, s), 3.53 (2H, s), 3.48 (1H, d).

Specific rotation (free base): $[\alpha]_D^{21.5} = +116.0°$ (C=0.2, H$_2$O):

EXAMPLE 25

Synthesis of 2'-deamino-2'-[1-(4-amino-2-pyrrolidonyl)]fortimicin B [the compound represented by the general formula (IV) wherein $R_3$ and $R_o$ form

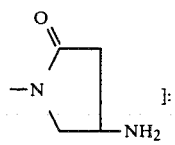

]:

1.7 g (2.5 mmoles) of 2'-N-α-[(s)-β-benzyl-N-benzyloxycarbonylaspartyl] fortimicin B obtained in the same manner as in Example 2 is dissolved in 20 ml of tetrahydrofuran. To the solution is added 20 ml (20 mmoles) of a diborane solution in tetrahydrofuran (1 mole solution of $BH_3$) under ice cooling. The temperature of the mixture is slowly brought back to room temperature and the mixture is stirred at the same temperature for 30 minutes. The reaction mixture is concentrated to dryness and the residue is dissolved in 40 ml of 0.2 N hydrochloric acid methanol. The mixture is allowed to stand at room temperature for 18 hours. To the reaction mixture is added 200 mg of 10% palladium carbon catalyst. Reductive hydrogenolysis is carried out at room temperature and at atmospheric pressure for 3 hours while blowing hydrogen gas through the mixture. The reaction mixture is subjected to filtration. The filtrate is concentrated and to the residue is added 40 ml of water. The solution is adjusted to pH 5.5 with 1 N sodium hydroxide. The solution is passed through a column (2 cm in inside diameter) packed with 100 ml of Amberlite CG-50 ($NH_4^+$ form) to adsorb the desired substance on the resin. The column is washed with 500 ml of water. Elution is carried out with 0.075 N aqueous ammonia. The eluate is taken in 20 ml fractions. The fraction Nos. 34–45 are combined and aqueous ammonia is removed therefrom by distillation to obtain 620 mg of a white powder. The powder has the following properties and is identified as the aboveindicated compound. Yield: 58.2%.

Rf value in silica gel TLC (developer:lower layer of chloroform:methanol:28% aqueous ammonia=1:1:1):0.69.

Nuclear magnetic resonance spectrum (in heavy water), δ(ppm)

a. free base (pD=11.4), 1.04 (3H, d), 2.36 (3H, s), 3.45 (3H, s), 5.20 (1H, d).

b. hydrochloride (DCl is added to free base, pD=1.0), 1.35 (3H, d), 2.81 (3H, s), 3.51 (3H, s), 5.36 (1H, d).

Mass spectrum (m/e): 432 ($M^+ +1$), 414, 393, 285, 235, 226, 207, 189, 126.

EXAMPLE 26

Synthesis of 2'-deamino-2'-[1-(4-benzyloxycarbonylamino-2-pyrrolidonyl)]-1,6'-di-N-benzyloxycarbonyl fortimicin B [the compound represented by the general formula (V) wherein $R_4$=—$COOCH_2C_6H_5$ and $R_3$ and $R_0$ form

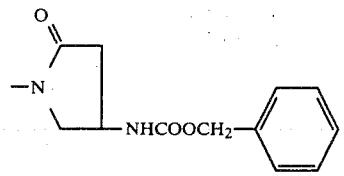

]:

720 mg (1.67 mmoles) of 2'-deamino-2'-[1-(4-amino-2-pyrrolidonyl)] fortimicin B obtained in the same manner as in Example 25 is dissolved in 30 ml of methanol. To the solution is added 1.37 g (5.51 mmoles) of N-benzyloxycarbonyloxysuccinimide and the mixture is stirred at room temperature for 4 hours. The reaction mixture is concentrated and the residue is dissolved in 2 ml of chloroform. The solution is passed through a column (1.5 cm in inside diameter) packed with 40 g of silica gel. Elution is carried out with chloroform:methanol=19:1. The eluate is taken in 20 ml fractions. The fraction Nos. 16–28 are combined and the solvent is removed therefrom by distillation to obtain 784 mg of a white powder. The powder has the following properties and is identified as the above-indicated compound. Yield: 56.4%.

Rf value in silica gel TLC (developer:chloroform:methanol=9:1):0.46.

Nuclear magnetic resonance spectrum (in methanol-$d_4$): δ(ppm): 1.09 (3H, d), 2.32 (3H, s), 3.47 (3H, s), 5.03 (6H, s), 7.32 (15H, s).

EXAMPLE 27

Synthesis of 2'-deamino-2'-[1-(4-amino-2-pyrrolidonyl)] fortimicin A [the compound represented by the general formula (I) wherein $R_0$ and R form

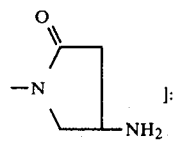

]:

230 mg (0.28 mmole) of 2'-deamino-2'-[1-(4-benzyloxycarbonylamino-2-pyrrolidonyl)]-1,6'-di-N-benzyloxycarbonyl fortimicin B obtained in Example 26 is dissolved in 4 ml of tetrahydrofuran. To the solution is added 110 mg (0.34 mmole) of 1-hydroxybenzotriazole ester of N-benzyloxycarbonylglycine and the mixture is allowed to react at room temperature for 18 hours. The reaction mixture is subjected to filtration. The filtrate is concentrated to dryness and to the residue are added 10 ml of 0.2 N-hydrochloric acid methanol and 40 mg of 10% palladium carbon catalyst. Reductive hydrogenolysis is carried out at room temperature and at atmospheric pressure for 4 hours while blowing hydrogen gas through the mixture. The catalyst is filtered off from the reaction mixture and the filtrate is concentrated. The concentrated filtrate is made up to 10 ml with water. The solution is adjusted to pH 5.5 with 1 N sodium hydroxide and is passed through a column (0.8 cm in inside diameter) packed with 10 ml of Amberlite CG-50 (NH$_4$+ form). After the column is washed with 100 ml of water, elution is carried out with 0.2 N aqueous ammonia. The eluate is taken in 5 ml fractions. The fraction Nos. 6–9 are combined. Aqueous ammonia is removed therefrom by distillation to obtain 92 mg of a white powder. The powder has the following properties and is identified as the above-indicated compound. Yield: 68.2%.

Rf value in silica gel TLC (developer:lower layer of chloroform:methanol:concentrated aqueous ammonia=1:1:1):0.67.

Nuclear magnetic resonance spectrum δ(ppm):
a. free base (in heavy water, pD=10.8): 1.04 (3H, d), 3.03 (3H, s), 3.44 (3H, s), 3.50 (2H, s), 3.65 (2H, m), 5.02 (1H, d).
b. hydrochloride (DCl is added to free base, pD=0.8): 1.35 (3H, d), 3.14 (3H, s), 3.47 (3H, s), 4.09 (2H, d), 5.09 (1H, d).

Mass spectrum (m/e): 488 (M+), 453, 403, 354, 264, 246, 226, 126, 97

Specific rotation: $[\alpha]_D^{21} = +131.5°$ (C=0.2, H$_2$O).

EXAMPLE 28

Synthesis of 2'-N-hydantoyl fortimicin B [the compound represented by the general formula (II) wherein R$_2$=—COCH$_2$NHCONH$_2$]

The same procedure as in Example 1 is repeated except that 5.2 g (1.4 moles per mole of the starting compound) of N-hydroxysuccinimide ester of hydantoic acid is used instead of 5.8 g of t-butyl-s-4,6-dimethyl-pyrimidine-2-ylthiocarbonate. From the fraction Nos. 46–60, 2.6 g of a white powder having the following properties is obtained and the powder is identified as the above-indicated compound. Yield: 34%.

Rf value in silica gel TLC:
a. developer:isopropanol:28% aqueous ammonia:chloroform=2:1:1, 0.44.
b. developer:lower layer of methanol:chloroform:28%, aqueous ammonia=1:1:1, 0.56.

Nuclear magnetic resonance spectrum (in heavy water): δ(ppm): 1.12 (3H, d), 1.2–1.8 (4H, m), 2.38 (3H, s), 3.47 (3H, s), 3.78 (2H, s), 5.28 (1H, d).

EXAMPLE 29

Synthesis of 2'-N-hydantoyl-1,6'-di-N-benzyloxycarbonyl fortimicin B [the compound represented by the general formula (III) wherein R$_2$=—COCH$_2$NHCONH$_2$ and R$_4$=—COOCH$_2$C$_6$H$_5$]

0.89 g of 2'-N-hydantoyl fortimicin B obtained in Example 28 is dissolved in 40 ml of methanol. To the solution is added 1.1 g (4.4 mmoles) of N-benzyloxycarbonyloxysuccinimide and the mixture is allowed to react at room temperature for 3 hours. The reaction mixture is concentrated and 10 ml of chloroform is added thereto. The chloroform solution is passed through a column (2 cm in inside diameter) packed with 40 g of silica gel. Elution is carried out with chloroform:methanol=19:1. The eluate is taken in 16 ml fractions. The fraction Nos. 18–58 are combined and the solvent is removed therefrom by distillation to obtain 0.95 g of a white powder. The powder has the following properties and is identified as the above-indicated compound. Yield: 66.3%.

Rf value in silica gel TLC:
a. developer:isopropanol:28% aqueous ammonia:chloroform=4:1:1, 0.64.
developer:lower layer of methanol:chloroform:14% aqueous ammonia=1:2:1, 0.43.

Nuclear magnetic resonance spectrum (in methanol-d$_4$): δ(ppm): 1.13 (3H, d), 1.2–1.9 (4H, m), 2.40 (3H, s), 3.50 (3H, s), 5.06 (4H, s), 5.33 (1H, d), 7.35 (10H, s).

EXAMPLE 30

Synthesis of 2'-N-hydantoyl fortimicin A (Compound 2) [the compound represented by the general formula (I) wherein R$_0$=H and R=—COCH$_2$NHCONH$_2$]

The same procedure as in Example 17 is repeated except that 490 mg (0.7 mmole) of 2'-N-hydantoyl-1,6'-di-N-benzyloxycarbonyl fortimicin B produced in Example 29 is used instead of 2'-N-[(s)-2-benzyloxycarbonylamino-4-hydroxybutyl]-1,6'-di-N-benzyloxycarbonyl fortimicin B. The obtained powder (240 mg) has the following properties and is identified as the abovein-dicated compound. Yield: 69.7%.

Rf value in silica gel TLC (developer:lower layer of chloroform:methanol:28% aqueous ammonia=1:1:1):0.41

Nuclear magnetic resonance spectrum (in heavy water): δ(ppm): 1.07 (3H, d), 1.2–1.8 (4H, m), 3.06 (3H, s), 3.45 (3H, s), 3.53 (2H, s), 3.84 (2H, s), 4.91 (1H, d).

Specific rotation (sulfate): $[\alpha]_D^{23} = +103.0°$ (C=0.2, H$_2$O).

EXAMPLE 31 (a synthesis process different from that of Example 3)

Synthesis of 2'-N-α-(N-benzyloxycarbonylasparaginyl) fortimicin B [the compound represented by the general formula (II) wherein $$R_2 = \underset{NHCOOCH_2C_6H_5}{-COCHCH_2CONH_2}]$$

(another process)

5.0 g (14.3 mmoles) of fortimicin B is dissolved in 140 ml of tetrahydrofuran:water=1:1 (by volume). To the solution is added 6.2 g (17.2 mmoles) of α-N-hydroxysuccinimide ester of N-benzyloxycarbonylasparagine and the mixture is allowed to react at room temperature for 6 hours. From the reaction mixture tetrahydrofuran is removed by distillation. After 70 ml of water is added to the residual aqueous solution, the solution is adjusted to pH 5.5 with 1 N sodium hydroxide. The solution is passed through a column (2.5 cm in inside diameter) packed with 150 ml of Amberlite CG-50 (NH$_4$+ form). The column is washed with 1 l of water. Elution is carried out with 0.1 N aqueous ammonia. The eluate is taken in 20 ml fractions. The fraction Nos. 24–58 are combined and aqueous ammonia is removed therefrom by distillation to obtain 1.8 g of a white powder. The powder has the following properties and is identified as the above-indicated compound. Yield: 21.2%.

Rf value in silica gel TLC (developer:lower layer of chloroform:methanol:14% aqueous ammonia=2:1:1):0.48.

Nuclear magnetic resonance spectrum (in methanol-d$_4$): δ(ppm): 1.04 (3H, d), 2.34 (3H, s), 2.4–2.9 (4H, m), 3.44 (3H, s), 4.92 (1H, d), 5.12 (2H, s), 7.33 (5H, s).

EXAMPLE 32

Sulfate of 2'-N-(-2,3-dihydroxypropyl) fortimicin A
(The other salts can be prepared in the same manner as this salt.)

80 mg of the free base of 2'-N-(2,3-dihydroxypropyl) fortimicin A obtained in Example 22 is dissolved in 0.2 ml of water. The solution is adjusted to pH 3 with 1 N sulfuric acid. The aqueous solution (about 0.3 ml) is dropwise added to 60 ml of ethanol with stirring. The resulting precipitate is isolated by filtration to obtain 95 mg of a white powder. The powder has the following properties and is identified as the above-indicated compound. Yield: 75.3%.

Elemental analysis: Calculated for $C_{20}H_{41}N_5O_8 \cdot 2H_2SO_4 \cdot C_2H_5OH \cdot 2H_2O$: C; 34.95%, H; 7.07%, N; 9.27%; Found: C; 35.14%, H; 7.21%, N; 9.08%.

What is claimed is:

1. 2'-N-substituted derivatives of fortimicin A represented by the formula:

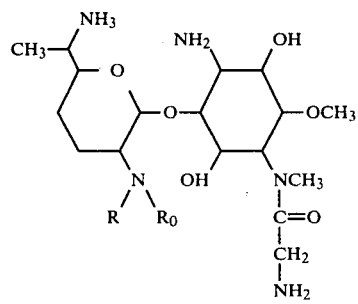

wherein $R_0$ represents a hydrogen atom or $R_0$ forms, together with a nitrogen atom and R, a substituted or unsubstituted 2-pyrrolidonyl group, wherein the substituents are 1~2 hydroxyl or amino groups and are bonded to the 3- or 4-position of the pyrrolidonyl group, and R represents —$COR_1$, —$CH_2R_1'$, —$CH(R_1')_2$ or an amidino group, wherein $R_1$ is an amino group, hydroxyaminoalkyl group wherein the hydroxy group and amino group are bonded to different carbon atoms or carbamoylaminoalkyl group wherein the alkyl groups are lower alkyl groups and $R_1'$ is a diaminoalkyl group, dihydroxyalkyl group, hydroxyaminoalkyl group wherein the hydroxy group and amino group are bonded to different carbon atoms, or guanidinoalkyl group wherein the alkyl groups are lower alkyl groups, and the pharmaceutically acceptable non-toxic acid addition salts thereof.

2. 2'-N-substituted derivatives of fortimicin A according to claim 1, wherein the derivatives are represented by the formula:

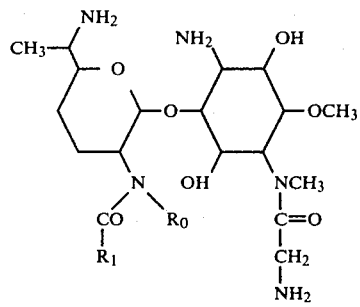

wherein $R_0$ and $R_1$ have the same significance as defined in claim 1 and the pharmaceutically acceptable non-toxic acid addition salts thereof.

3. 2'-N-substituted derivatives of fortimicin A according to claim 1, wherein the derivatives are represented by the formula:

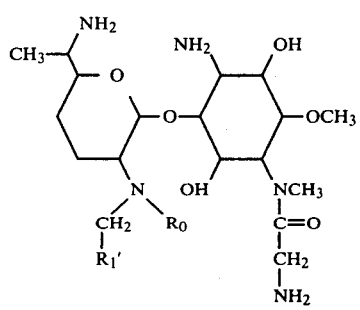

wherein $R_0$ and $R_1'$ have the same significance as defined in claim 1 and the pharmaceutically acceptable non-toxic acid addition salts thereof.

4. 2'-N-substituted derivatives of fortimicin A according to claim 1, wherein the derivatives are represented by the formula:

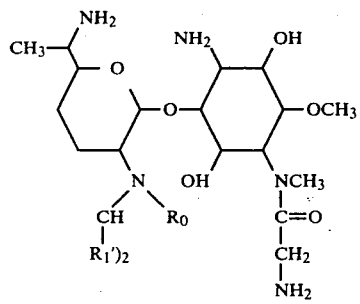

wherein $R_0$ and $R_1'$ have the same significance as defined in claim 1 and the pharmaceutically acceptable non-toxic acid addition salts thereof.

* * * * *